United States Patent [19]

Sylvester

[11] Patent Number: 5,112,470
[45] Date of Patent: May 12, 1992

[54] ELECTROPHORESIS APPARATUS

[75] Inventor: Keith V. Sylvester, Del Mar, Calif.

[73] Assignee: Stratagene, La Jolla, Calif.

[21] Appl. No.: 624,074

[22] Filed: Dec. 7, 1990

[51] Int. Cl.$^5$ .................. G01N 27/28; G01N 27/26
[52] U.S. Cl. ........................ 204/299 R; 204/182.8
[58] Field of Search .................. 204/182.8, 299 R

[56] References Cited

U.S. PATENT DOCUMENTS

| | | | |
|---|---|---|---|
| 4,574,040 | 3/1986 | Delony et al. | 204/182.8 |
| 4,773,984 | 9/1988 | Flesher et al. | 204/182.8 |
| 4,800,010 | 1/1989 | Hellman, Jr. | 204/182.8 |
| 4,802,969 | 2/1989 | Hellmann, Jr. | 204/182.8 |
| 4,828,669 | 5/1989 | Hellmann, Jr. | 204/182.8 |
| 4,957,613 | 9/1990 | Schuette | 204/182.8 |
| 5,013,420 | 5/1991 | Schuette | 204/182.8 |

Primary Examiner—John Niebling
Assistant Examiner—David G. Ryser
Attorney, Agent, or Firm—Bingham & Fitting

[57] ABSTRACT

A vertically oriented gel electrophoresis apparatus having a support structure for supporting in a generally vertical plane a gel plate assembly, including a pair of upright side members, a support plate lying in a vertical plane and extending between the side members, a lower buffer tank for supporting the gel plate assembly between the side members, and an upper buffer tray having a sealing gasket on one side thereof which is engageable with the gel plate assembly adjacent the upper edge thereof upon movement of the upper tray into engagement with the gel plate assembly, to seal against leakage of buffered solution disposed in the upper tray. The upper tray is moved into sealing engagement with the gel plate assembly and away therefrom by a cam disposed in cam slots in the sides of the upper tray and operated by a handle disposed externally of the side members and connected to the cam by a shaft passing through the side members. The buffer solution in the upper tray can be drained therefrom by a drain system connected through the bottom of the upper tray and connected to a portion of the lower tank. Roller retainer or locking members are slidably received by each of the side members and include a roller having resilient surface for engagement with the surface of the gel plate assembly for retaining the gel plate assembly in position against the support plate thereby minimizing mechanical stress. The gasket attached to the upper tray is configured with ribs and compartments to minimize the extent of leakage, and includes a portion positioned over the top of one of the plates of the gel plate assembly as well as portions enclosing sides thereof adjacent the upper end.

22 Claims, 4 Drawing Sheets

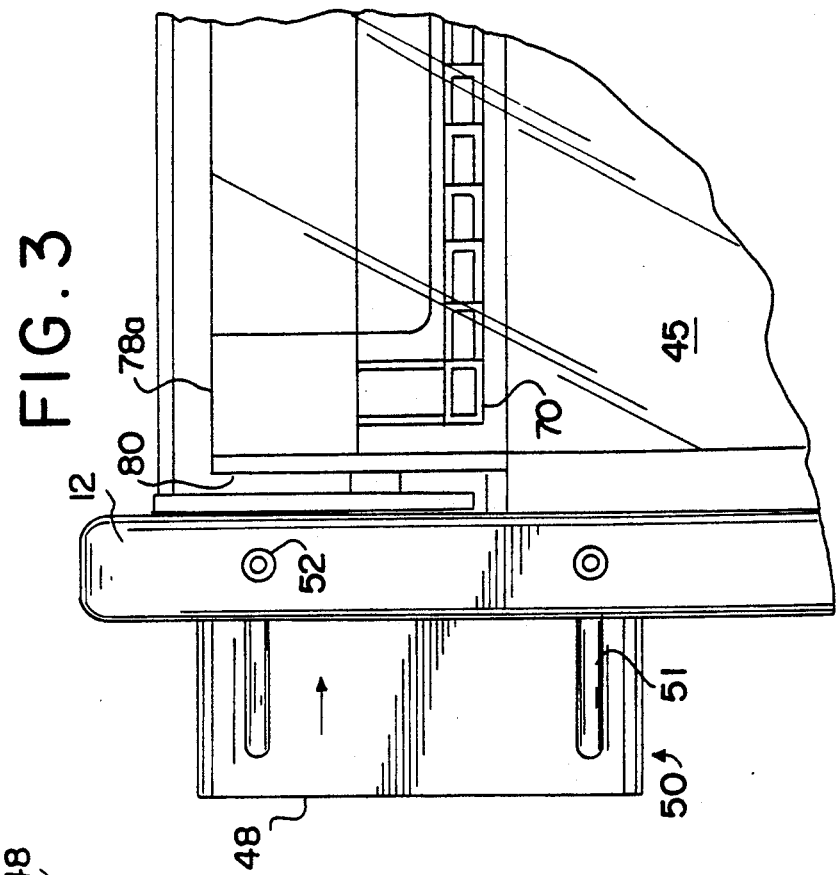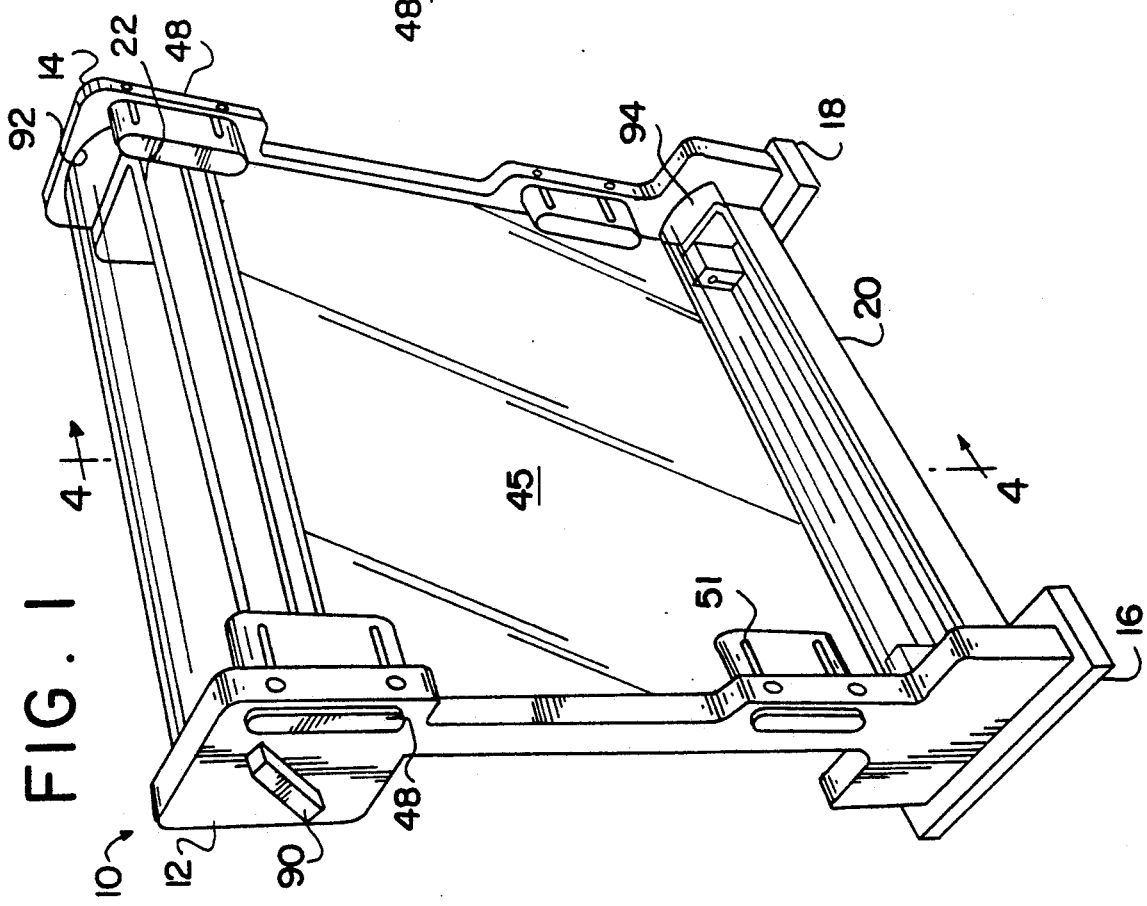

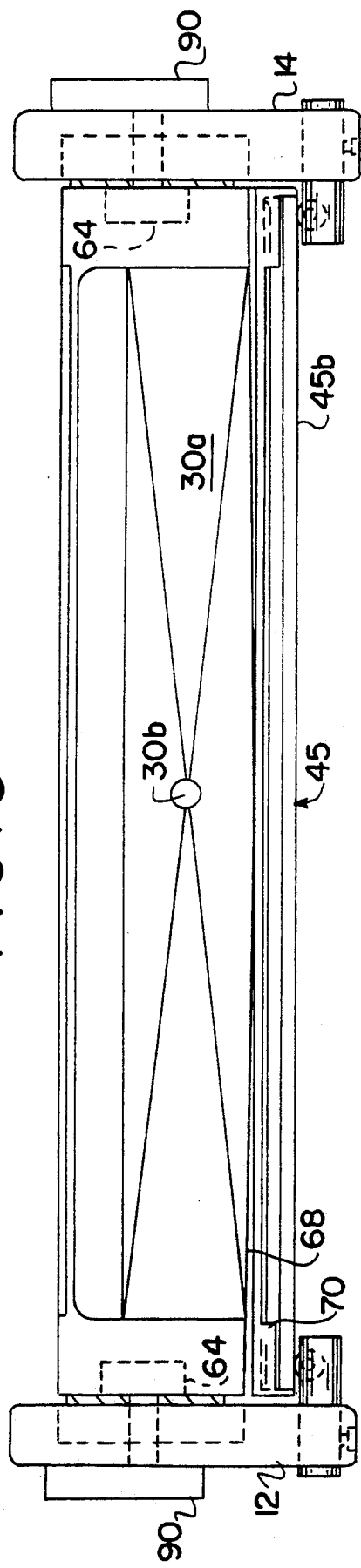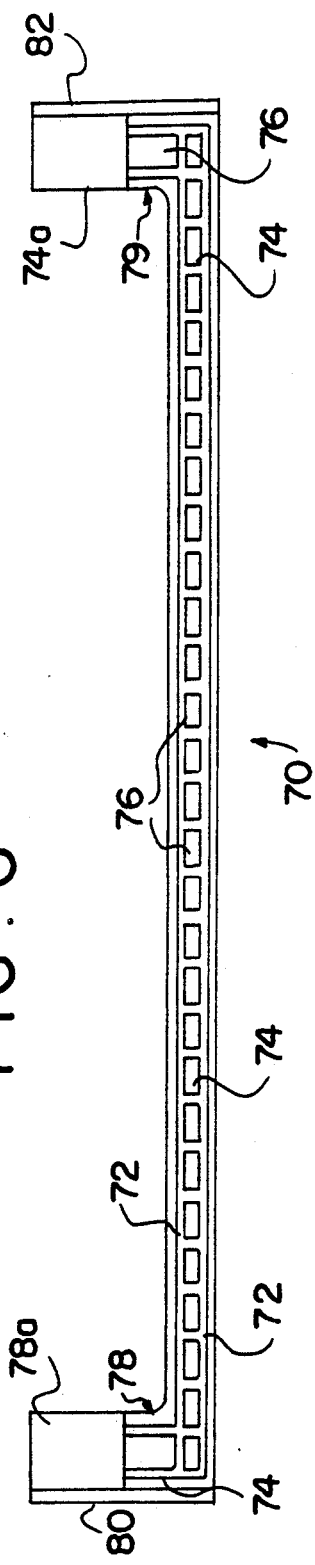

ELECTROPHORESIS APPARATUS

FIELD OF THE INVENTION

The present invention relates to gel electrophoresis apparatus and in particular to a vertically oriented device for use in conjunction with nucleic acid sequencing.

BACKGROUND OF THE INVENTION

Gel electrophoresis processes are time consuming, in part because it is important to insure that no defects or errors occur during processing. There are a variety of configurations and apparatus for achieving and performing such processes. One form of such an apparatus which is desirable, at least in part because of its space-saving configuration, is to orient the gel plate assembly used in such devices vertically. In this regard, it is necessary to provide an electrical connection between the electrodes connected to a power source and the edges of the vertically oriented gel plate assembly. This is accomplished by locating electrodes in a buffer solution which make intimate contact with the gel disposed between the plates of the gel plate assembly.

It is important that such devices be constructed to prevent leakage of the buffer solutions. In addition, it is also important to minimize mechanical stresses imposed on the gel plate assembly or sandwich while simultaneously ensuring proper spacing and positioning of the assembly in the apparatus.

It would be desirable to construct the gel plate assembly of planar members to facilitate setup and preparation of the components of the apparatus. Planar plates could also reduce the costs of the component which is most likely to require replacement, namely the gel plates themselves. Furthermore, the ability to quickly and easily dispose of the buffer solutions after use would also improve the efficiency of the operation and increase the ease of operation of such apparatus.

SUMMARY OF THE INVENTION

In accordance with the present invention, there is provided a gel electrophoresis apparatus capable of being used, for example, for nucleic acid sequencing. Apparatus in accordance with the present invention takes the form of a vertically oriented device designed to prevent buffer leakage, to minimize stress cracking of the plates of the gel plate assembly, and to alleviate the difficulties of disposing buffer solutions utilized in the electrophoresis process.

Apparatus incorporating the present invention includes a support structure for supporting a gel plate assembly in a generally vertical plane. In apparatus incorporating the present invention, a gel plate assembly is comprised of a pair of generally planar spaced apart gel plates. The support structure includes a pair of side members between which is disposed the gel plate assembly retained in position against a support plate oriented generally in a vertical plane and extending between the side members.

Retaining means associated with the side members are selectively operable and engageable with the gel plate assembly over a surface thereof for retaining the gel plate assembly in place between the retaining means and the support plate.

The apparatus includes a lower buffer tank and support member positioned between the side members for supporting the bottom edge of the gel plate assembly in position within the support structure. The lower buffer tank member is adapted to contain a buffer solution which makes contact with the bottom edge of the gel plate assembly, and the gel disposed between the plates thereof.

A movable upper tray member is supported between the side members adjacent the upper edge of the gel plate assembly for movement towards the gel plate assembly into leak resistant sealing engagement therewith adjacent the upper edge thereof. A buffer solution disposed in the upper tray contacts the gel plate assembly and the gel disposed between the plates thereof for providing the necessary electrical path between electrode in contact with the buffer solution in upper tray as required for implementation of the electrophoresis process.

Thus, in apparatus incorporating the present invention, the gel plate assembly is retained in place by retaining means which exert pressure over surface areas of the gel plate assembly to minimize stress and resultant stress related cracking. In addition, the movable upper buffer tray member facilitates the use of a simplified gel plate assembly configuration in the form of planar members, and is capable of providing the desired leak-resistant seal to prevent leakage of the buffer solution from the tray when positioned against the upper edge of the gel plate assembly.

In accordance with one embodiment of the present invention, the upper buffer tray assembly is reciprocally movable towards and away from the gel plate assembly by use of a cam disposed in the walls of the upper tray. Each cam is operable upon rotation of a handle attached thereto and accessible externally of the support structure for moving the upper buffer tray towards and into sealing engagement with the gel plate assembly.

The upper buffer tray is a three-sided container, the fourth side of which is provided by gel plate assembly when the upper tray is moved into leak-resistant sealing engagement therewith. Sealing means in the form of a gasket is provided on the lateral open-sided face of the upper buffer tray and is engageable with the gel plate assembly for effectuating the desired leak-resistant seal between the upper buffer tray and the gel plate assembly.

In accordance with the present invention, the leak-resistant seal is enhanced by the configuration of the sealing gasket. The gasket includes a plurality of intersecting ribs which define hollow recesses or compartments therebetween. The use of the ribs is to improve the sealing characteristics of the gasket. The transverse ribs define a series of generally liquid-tight compartments which are to limit the extent of any leakage of the buffer solution that does occur. Thus, the combination of the horizontal and vertical ribs formed in the surface of the sealing gasket improves the seal and inhibits movement of any leaking buffer solution, thereby restricting the leakage.

In accordance with another aspect of the present invention, in order to ensure a good seal throughout the entire extent and width of the upper tray, the front edge of the tray may be formed slightly convex in order to increase the sealing pressure at the center of the gasket where leakage is more likely to occur than at the edges. Furthermore, the gasket is configured to seal the upper edge and the outer lateral edges of the gel plate assembly adjacent the sides thereof in order to further inhibit the likelihood of leakage occurring.

The gel plate assembly is retained in the support structure by a plurality of roller clamp assemblies, each including a clamp member slidably supported in each of the side frames. Each of the slidable roller clamp assemblies includes a pressure member in the form of a roller oriented along a vertical axis transverse to the sliding movement of the slidable clamps. The surface of the rollers can take the form of any suitable resilient material to provide sufficient force to hold the glass plate in place while minimizing the stresses imposed on the gel plate assembly itself. The roller clamp assemblies allow for proper positioning and retention of the gel plate assembly while simultaneously minimizing stresses thereon by distribution of the pressure over the surface of the clamp rollers without imparting to the assembly some of the stresses that have been previously produced, e.g., by clips.

In order to dispose of the buffer solution, the upper buffer tray includes a drain suitably connected to a portion of the lower tank for draining the buffer solution from the upper tray into the lower tank prior to removal of the gel plate assembly. The buffer solution is drained by opening a valve connected to the upper tray drain and allowing the solution to drain completely therefrom into a suitable receptacle, such as a closed portion of the lower buffer tank wherein the solution can be disposed of or handled as desired.

Such disposal of the solution occurs with minimal leakage and allows for removal of the gel plate assembly by retracting of the upper tray and the roller clamps and removal of the plate assembly for further processing in accordance with known techniques.

Numerous other advantages and features of the present invention will become readily apparent from the following detailed description of the invention and the embodiments thereof, from the claims, and from the accompanying drawings in which the details of the invention are fully and completely disclosed as a part of this specification.

BRIEF DESCRIPTION OF THE DRAWINGS

FIG. 1 is a perspective view of an apparatus incorporating the present invention;

FIG. 3 (with FIG. 1) is a plan enlarged front view of a portion thereof:

FIG. 5 is a top view thereof;

FIG. 6 is a front view of a gasket taken along line 6—6 of FIG. 2; and

DETAILED DESCRIPTION OF PREFERRED EMBODIMENTS

Figure 2:
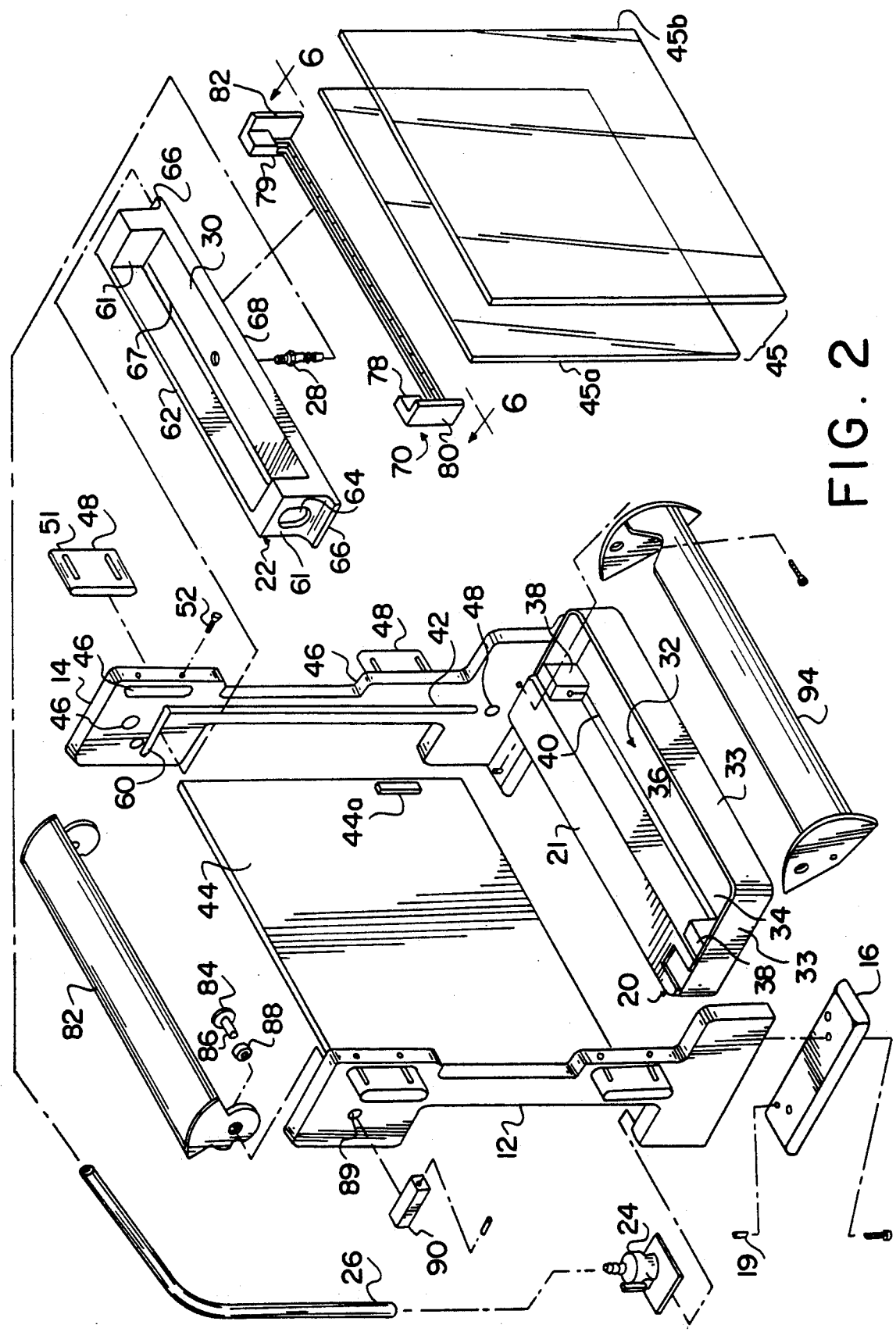
FIG. 2 is an exploded view of the apparatus of FIGURE 1.
Figure 4:
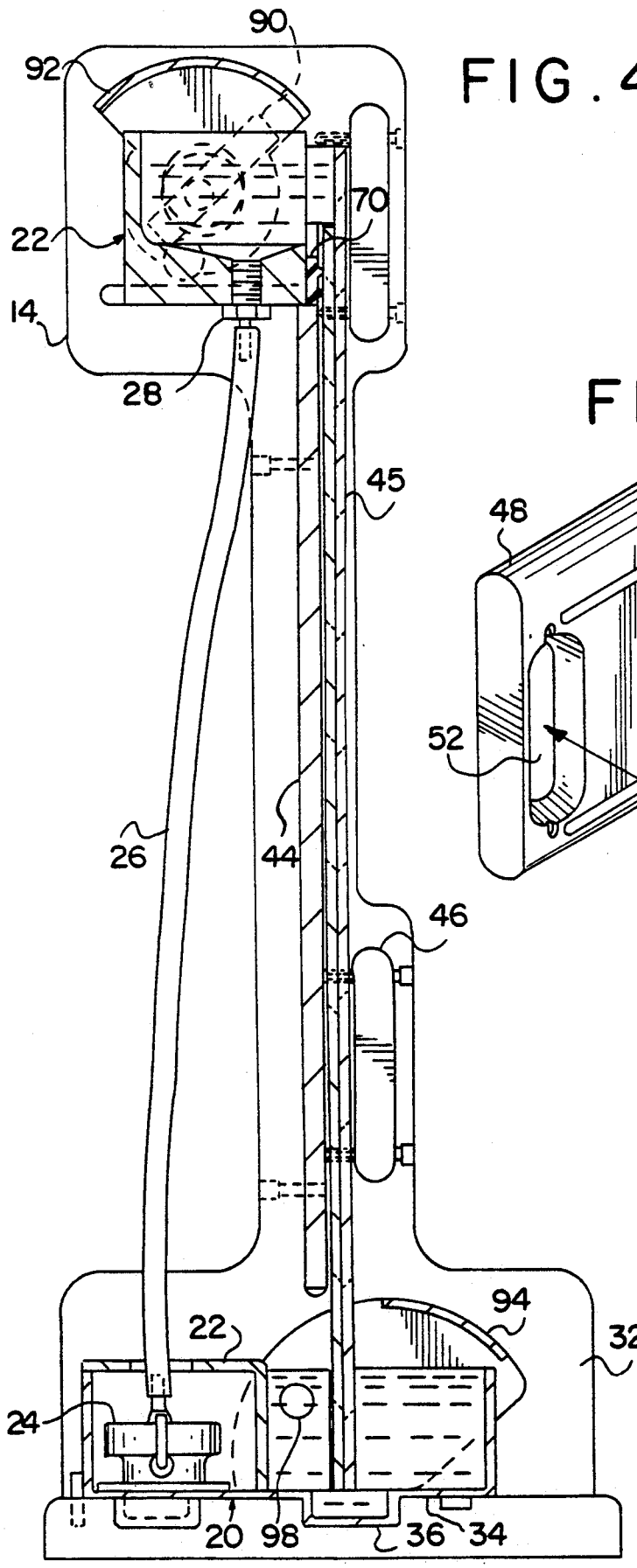
FIG. 4 is a sectional view taken along lines 4—4 of FIGURE 1.
Figure 7:
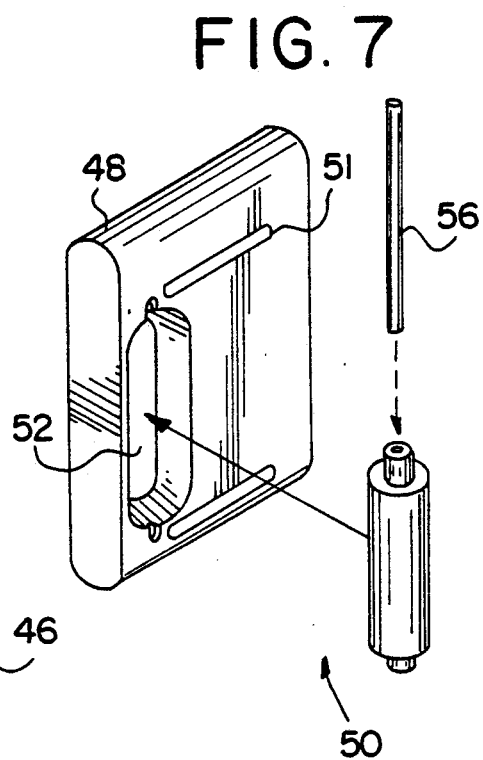
FIG. 7 is an exploded view of a roller clamp assembly.

While this invention is susceptible of embodiment in many different forms, there is shown in the drawing and will be described herein in detail, a specific embodiment thereof, with the understanding that the present disclosure is to be considered as an exemplification of the principles of the invention and is not intended to limit the invention to the specific embodiment illustrated.

The electrophoresis apparatus 10 incorporating the present invention includes a pair of side members or uprights 12, 14 which are substantial mirror images of each other. Each of the uprights 12, 14 is supported on a foot 16, 18 in a generally vertical plane. The feet 16, 18 include dowel pegs 19 for receiving and positioning a lower buffer tray or tank 20. The lower tank 20 includes a covered rear portion 21 for receiving buffer solution drained from an upper buffer tray 22 through a drain valve 24 and a drain tube 26 connected to a drain fitting 28 inserted in the bottom wall 30 of upper buffer tray 22. The lower buffer tank 20 also includes a forward open portion 32 defined by walls 33, the front of covered portion 21 and a bottom 34. The bottom may include a well 36. A pair of electrode blocks 38 are located in the forward open portion 32 of the lower tank 20, and an electrode wire 40 extends between the blocks 38 for contact with a buffer solution placed in the forward open portion 32 of tank 20.

Each of the side members 12, 14 includes a vertically extending elongated slot 42. The slots 42 receive the side edges of a thermal support plate 44 which is retained in the slots and provides a thermal sink and a support for the gel plate assembly 45 described below. The support plate 44 may include alignment members 44a. Each of the uprights also includes a pair of vertical openings 46, each of which is designed to receive and slidably support a roller clamp member 48 each forming part of a roller clamp assembly support 50.

Each roller clamp member 48 includes a pair of lateral slots 51 engaged by support pins 52 extending through the front of the uprights 12, 14 for slidable movement of the clamp member 48 through the uprights 12, 14 to retain the gel plate assembly 45 in position within the frame against the thermal support plate 44. Each of the roller clamp members 48 includes a generally vertically oriented roller receiving recess 54 into which is disposed a clamp roller 55 rotatably supported on an axle 56 oriented vertically to facilitate clamping and retention of a gel plate assembly 45 in place within the apparatus 10.

The surface of the rollers 50 are preferably soft and resilient. If a hard core is utilized, the surface may be covered, for example, with a latex surgical tubing, to provide the desired soft surface for engagement with the surface of the gel plate assembly 45.

Typically, the unflexed or relaxed dimension between the soft surface of the clamp rollers 55 and the surface of the support plate 44 is less than the thickness of the gel plate assembly 45 whereby the resilient surface of the rollers 55 provide effective clamping and retention of the plate over the vertical extent of the roller without introduction of stresses which could very well result in cracking of the plates of the gel plate assembly during use.

As illustrated, each upright includes two roller clamps 48 that are transversely movable inwardly for retaining the gel plate assembly 45 in position, and outwardly to release the gel plate assembly for removal or installation.

Each of the uprights 12, 14 includes a lateral or generally horizontal transverse groove 60 extending rearwardly from the upper edge of the support plate slot 42 for slidably receiving and supporting the upper buffer tray 22. The upper buffer tray 22 is formed as a generally three-sided structure having the bottom wall 30, a pair of opposed sidewalls 61 and a rearwall 62 to define a receptacle in conjunction with the gel plate assembly 45 for receiving and retaining a buffer solution.

The sides 61 of the upper buffer tray 22 include a vertically elongated cam slot 64 formed therein. The bottom edges of the sidewalls 61 flare outwardly to define flanges 66 which are received in the transverse grooves 60 in each of the uprights 12, 14. The top surface 30a of the bottom wall 30 is tapered toward a drain hole 30b in the center of the bottom wall which receives the drain fitting 28 connected to the drain tube 26 for selectively draining buffer solution from the upper tray 22 as desired. An electrode 67 is disposed in tray 22.

The front surface 68 of the upper tray 22 is generally convex when observed from above in order to secure a good leak-resistant seal between the upper tray 22 and the gel plate assembly 45. The front surface of the upper buffer tray is affixed to a U-shaped gasket 70 which is suitably attached to the surface such as by an appropriate adhesive. The gasket is composed of VISILOX V-225 compound produced by Visilox Systems, Inc., of Poestenkill, N.Y., having 30% silicone fluid such as VISILOX's VSI V-50 to a Durometer of 20±5. As shown in FIGS. 3 and 6, the front surface of the gasket 70 is composed of a pair of horizontal ribs 72 and a plurality of vertical ribs 74 to define a plurality of liquid-type compartments 76 therein to inhibit leakage and to limit leakage from one side of the gasket to another in the event any such leakage does occur.

The upper ends 78a, 79a of the legs of the U-shaped gasket 70 are thicker to define an undercut for receiving one of the plates 45a of the gel plate assembly 45 therein to provide a seal therebetween. The second plate 45b of the gel plate assembly 45 extends above the first plate 45a. The surface of second plate 45b engages the upper thicker portions 78a, 79a of the legs 78, 79 of the gasket 70 to provide a seal therebetween. The gasket 70 further includes an external side flanges 80, 82 which surround and extend over the side edges of the gel plate assembly 45 to prevent leakage therebetween. Thus, the gasket 70 provides a seal along the upper edge of at least the first inner shorter plate 45a of the gel plate assembly 45 and provides access for the buffer in the upper buffer tray 22 to the gel disposed between the plates of the gel plate assembly 45.

Each of the vertically elongated cam slots 64 in the sidewalls 58, 60 of the upper tray 22 receives a cam 84 therein having an offset cam shaft 86 passing through a bushing 88 and through a corresponding aperture 89 in each of the uprights, 12, 14. A handle or cam lever 90 is affixed to each cam shaft 86. Rotation of the handles 90 effects rotation of the off-center cams 84 and thereby effectuates a transverse sliding movement of the upper buffer tray 22 towards and away from the gel plate assembly 45 for effectuating the desired leak-resistant seal between the gasket 70 attached to the inner surface of the upper buffer tray 22 and the surfaces of the gel plate assembly 45.

The gel plate assembly 45 is inserted into the support structure and is positioned in the lower buffer tank adjacent to the electrode blocks 38 over the well 36 formed in the bottom 34 of the tank 20 to ensure that there is adequate contact between the buffer solution in the bottom tank 10 and the gel located between the plates 45a, 45b of the gel plate assembly 45. When the gel plate assembly 45 is positioned in the bottom tray, it is pivoted forward against the thermal support plate 44 between locating members 44a. The roller clamps 48 slidably supported in each of the uprights are moved inwardly so the soft surface rollers 55 engage the outer or front surface of the gel plate assembly 45 and provide sufficient pressure over an area of the plate assembly to retain it in place.

The cam levers 90 are rotated to shift the upper buffer tray 22 and the gasket 70 attached to the front surface thereof into sealing engagement with the shorter plate 45a of the gel plate assembly 45. The upper edge of shorter plate 45a fits within the undercut of the side legs 78, 79 of the gasket 70. The upper thicker portions 78a, 79a of the legs 78, 79 of the U-shaped gasket 70 engage the surface of the longer plate 45b and the sides 80, 82 engage the side edges of the plate assembly 45 to produce the leak-resistant seal therebetween. The buffer solution introduced into the upper tray 22 makes contact with the gel between the plates of the gel plate assembly 45.

A pair of upper and lower safety covers 92, 94 are pivotably supported between the uprights 12, 14 and have side portions therein which cover upper and lower electrode apertures 96, 98 formed in one of the uprights 14. Until the safety covers 90, 92 are closed, the sides of the covers block the electrode apertures 94, 96 and preclude introduction of the electrode into contact with the electric wires located within the upper tray 22 and lower tank 20.

Thus, there has been disclosed a vertically oriented device capable of performing gel electropohoresis such as nucleic acid sequencing in which a gel plate assembly can be constructed of planar plates and inserted into the apparatus, in which the upper buffer tray is movable into contact with the gel plate assembly seal, in which the gel plate assembly is retained in place by suitable roller clamps to minimize pressure by distributing the clamping pressure over an area of the plate in a manner that minimizes the stress, and in which the buffer solution in the upper buffer tray can be removed easily and simply without fuss.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the appended claims.

What is claimed is:

1. A vertically oriented gel electrophoresis apparatus comprising:
   a support structure for supporting in a generally vertical plane a gel plate assembly comprised of a pair of generally planar, spaced apart plates, said support structure including:
   a pair of side members between which is disposed said gel plate assembly;
   a support plate lying generally in a vertical plane and extending between said side members;
   retaining means associated with said side members and selectively engageable with said gel plate assembly for retaining said gel plate assembly in place between said retaining means and said support plate;
   a lower tank member positioned between said side members for supporting the bottom edge of said gel plate assembly in position in said support structure, said lower tank member adapted to contain a buffer solution in contact with the bottom edge of said gel plate assembly and the gel disposed between said generally planar plates thereof;
   an upper tray member supported between said side members adjacent the upper edge of said gel plate assembly for movement towards and for selective sealing engagement of said gel plate assembly adjacent the upper edge thereof, said upper tray member adapted to contain a buffer solution in contact with the upper edge of said gel plate assembly and the gel disposed between said generally planar plates thereof; and electrode means in circuit making contact with said buffer solutions in said upper tray and said lower tank for completing a circuit between said electrodes through said gel plate assembly.

2. An apparatus as claimed in claim 1 wherein:
one side of said upper tray member is engageable against one side of said gel plate assembly adjacent the upper edge thereof in response to movement of said upper tray member towards said gel plate assembly to provide a seal therebetween and prevent leakage therefrom of said buffer solution.

3. An apparatus as claimed in claim 2 including:
sealing means disposed between said one side of said upper tray member and said gel plate assembly to effectuate said seal therebetween in response to movement of said upper tray member into engagement with said gel plate assembly.

4. An apparatus as claimed in claim 3 wherein:
the upper edge of said sealing means is generally co-planar with the bottom of the support tank member and the upper edge of one of said gel plate assembly's spaced apart plates facing said sealing means over a major extent of said sealing means.

5. An apparatus as claimed in claim 4 wherein:
said sealing means includes a portion on either side that overlaps the upper edge of said facing plate of said gel plate assembly.

6. An apparatus as claimed in claim 5 wherein:
said sealing means includes a side portion on each side that overlaps the side edges of said gel plate assembly adjacent the upper edge thereof.

7. An apparatus as claimed in claim 3 wherein:
the upper edge of the plate of said gel plate assembly facing said upper tray member terminates below the upper edge of the other plate of said gel plate assembly.

8. An apparatus as claimed in claim 7 wherein:
the upper edge of said sealing means is generally co-planar with the bottom of the support tank member and the upper edge of one of said gel plate assembly's spaced apart plates over a major extent of said sealing means.

9. An apparatus as claimed in claim 8 wherein:
said sealing means includes a portion on either side that overlaps the upper edge of said facing plate of said gel plate assembly.

10. An apparatus as claimed in claim 9 wherein:
said sealing means includes a side portion on each side that overlaps the side edges of said gel plate assembly adjacent the upper edge thereof.

11. An apparatus as claimed in claim 3 wherein said sealing means is attached to and is carried by said one side of said upper tray member.

12. An apparatus as claimed in claim 3 wherein:
at least a portion of the surface of said sealing means engageable with said gel plate assembly is comprised of a plurality of ribs defining compartments therebetween for effectuating said seal between said sealing means and said gel plate assembly.

13. An apparatus as claimed in claim 2 wherein said one side of said upper tray member is convex.

14. An apparatus as claimed in claim 1 wherein said retaining means associated with each of said side members comprises a plurality of rollers engageable with the surface of said gel plate assembly for retaining said assembly in place between said support plate and said retaining means.

15. An apparatus as claimed in claim 14 wherein each of said retaining means includes a roller support member slidably received in each of said side members and movable between an outer retracted position permitting installation and removal of said gel plate assembly and an inner retaining position in which the roller supported thereby engages the surface of said gel plate assembly for retaining said gel plate assembly in place.

16. An apparatus as claimed in claim 15 wherein the surface of said rollers is comprised of a resilient material engageable with the surface of said gel plate assembly over an area thereof.

17. An apparatus as claimed in claim 1 including a drain in the bottom of said upper tray member, means for connecting said drain to a receptacle to selectively drain the buffer solution from said upper tray.

18. An apparatus as claimed in claim 17 wherein said drain receptacle is formed as a portion of said lower tank member.

19. An apparatus as claimed in claim 18 wherein said drain receptacle is separate from the buffer solution containing portion of said lower tank member.

20. An apparatus as claimed in claim 19 wherein said drain includes a manually operable valve for gravity draining said upper tray member.

21. An apparatus as claimed in claim 1 including handle means accessible externally of said support structure and connected to said upper tray member, said handle means being operable to effect said movement of said upper tray member towards said gel plate assembly to effect said sealing engagement therewith.

22. An apparatus as claimed in claim 1 wherein said upper tray member includes slot means in the opposite sides thereof, and including:
cam members disposed in each of said slot means; and
cam shaft means connecting each of said cam members to a handle means located externally of the corresponding one of said side members;
each said handle means being rotatable to rotate said cam means located in a corresponding one of said slot means to effect said movement of said upper tray member towards said gel plate assembly.

* * * * *